United States Patent
Goosen et al.

(10) Patent No.: US 8,634,899 B2
(45) Date of Patent: Jan. 21, 2014

(54) MULTI MODE IMAGING MARKER

(75) Inventors: Ryan L. Goosen, Coopersville, MI (US);
Steven E. Field, Grand Rapids, MI (US);
Richard M. Chesbrough, Bloomfield Hills, MI (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

(21) Appl. No.: 11/275,919

(22) Filed: Feb. 3, 2006

(65) Prior Publication Data

US 2006/0173280 A1   Aug. 3, 2006

Related U.S. Application Data

(63) Continuation of application No. 10/709,899, filed on Jun. 4, 2004, now abandoned, and a continuation-in-part of application No. 10/707,044, filed on Nov. 17, 2003, now Pat. No. 7,424,320.

(51) Int. Cl.
*A61B 5/05* (2006.01)

(52) U.S. Cl.
USPC ............ 600/431; 600/414; 600/424; 600/426

(58) Field of Classification Search
USPC .......... 600/414, 420, 426, 431, 458, 432, 424
See application file for complete search history.

(56) References Cited

U.S. PATENT DOCUMENTS

| | | |
|---|---|---|
| 2,899,362 A | 8/1959 | Sieger, Jr. et al. |
| 2,907,327 A | 10/1959 | White |
| 3,402,712 A | 9/1968 | Eisenhand |
| 3,516,412 A | 6/1970 | Ackerman |
| 3,818,894 A | 6/1974 | Wichterle et al. |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |

(Continued)

FOREIGN PATENT DOCUMENTS

| | | |
|---|---|---|
| DE | 1029528 B | 5/1958 |
| EP | 0146699 A1 | 7/1985 |

(Continued)

OTHER PUBLICATIONS

Press release for Biopsys Ethicon Endo-Surgery (Europe) GmbH; The Mammotome Vacuum Biopsy System. From: http://www.medicine-news.com/articles/devices/mammotome.html. 3 pages.

(Continued)

*Primary Examiner* — Parikha Mehta

(57) ABSTRACT

The invention provides a device for percutaneously implanting an imaging marker for identifying a location within a tissue mass. The subcutaneous imaging marker comprises at least a first element and a second element, each of which have a primary imaging mode. The primary imaging mode of the first element is different from that of the second element.

7 Claims, 5 Drawing Sheets

(56) References Cited

U.S. PATENT DOCUMENTS

| | | | |
|---|---|---|---|
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,018,530 A | 5/1991 | Rank et al. |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,100 A | 6/1994 | Herweck et al. |
| 5,320,613 A | 6/1994 | Houge et al. |
| 5,328,955 A | 7/1994 | Rhee et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,358,677 A | 10/1994 | Muth et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,458,643 A * | 10/1995 | Oka et al. .................. 623/17.16 |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,665,092 A | 9/1997 | Mangiardi et al. |
| 5,667,767 A | 9/1997 | Greff et al. |
| 5,669,882 A | 9/1997 | Pyles |
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,716,981 A | 2/1998 | Hunter et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |

(56) References Cited

U.S. PATENT DOCUMENTS

| | | |
|---|---|---|
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 * | 5/2001 | Barsch ............ 128/897 |
| 6,241,687 B1 | 6/2001 | Voegele et al. |
| 6,241,734 B1 | 6/2001 | Scribner et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 * | 4/2002 | Sirimanne et al. ............ 600/3 |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,423,252 B1 | 7/2002 | Chun et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,447,524 B1 | 9/2002 | Knodel et al. |
| 6,447,527 B1 | 9/2002 | Thompson et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,567,689 B2 | 5/2003 | Burbank et al. |
| 6,575,888 B2 | 6/2003 | Zamora et al. |
| 6,575,991 B1 | 6/2003 | Chesbrough et al. |
| 6,585,773 B1 | 7/2003 | Xie |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,628,982 B1 | 9/2003 | Thomas et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,662,041 B2 | 12/2003 | Burbank et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,881,226 B2 | 4/2005 | Corbitt, Jr. et al. |
| 6,899,731 B2 | 5/2005 | Li et al. |
| 6,918,927 B2 | 7/2005 | Bates et al. |

(56) References Cited

U.S. PATENT DOCUMENTS

| | | |
|---|---|---|
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,992,233 B2 | 1/2006 | Drake et al. |
| 6,993,375 B2 | 1/2006 | Burbank et al. |
| 6,994,712 B1 | 2/2006 | Fisher et al. |
| 6,996,433 B2 | 2/2006 | Burbank et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,047,063 B2 | 5/2006 | Burbank et al. |
| 7,083,576 B2 | 8/2006 | Zarins et al. |
| 7,125,397 B2 | 10/2006 | Woehr et al. |
| 7,160,258 B2 | 1/2007 | Imran et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,329,414 B2 | 2/2008 | Fisher et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 | 8/2009 | Chesbrough et al. |
| 7,577,473 B2 | 8/2009 | Davis et al. |
| 7,637,948 B2 | 12/2009 | Corbitt, Jr. |
| 7,651,505 B2 | 1/2010 | Lubock et al. |
| 7,736,671 B2 | 6/2010 | DiCarlo et al. |
| 7,877,133 B2 | 1/2011 | Burbank et al. |
| 8,012,454 B2 | 9/2011 | Rioux et al. |
| 2001/0006616 A1 | 7/2001 | Leavitt et al. |
| 2002/0004060 A1 | 1/2002 | Heublein et al. |
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1* | 5/2002 | Hoshino et al. .............. 600/423 |
| 2002/0058882 A1 | 5/2002 | Fulton, III et al. |
| 2002/0077687 A1 | 6/2002 | Ahn |
| 2002/0082517 A1 | 6/2002 | Klein |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0151796 A1 | 10/2002 | Koulik |
| 2002/0165608 A1 | 11/2002 | Llanos et al. |
| 2002/0177776 A1 | 11/2002 | Crawford Kellar et al. |
| 2002/0188196 A1* | 12/2002 | Burbank et al. .............. 600/431 |
| 2002/0193815 A1* | 12/2002 | Foerster et al. .............. 606/151 |
| 2002/0193867 A1 | 12/2002 | Gladdish, Jr. et al. |
| 2003/0032969 A1 | 2/2003 | Gannoe et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1* | 10/2003 | Ferrera et al. .............. 606/151 |
| 2003/0225420 A1 | 12/2003 | Wardle |
| 2003/0233101 A1 | 12/2003 | Lubock et al. |
| 2003/0236573 A1 | 12/2003 | Evans et al. |
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0068312 A1 | 4/2004 | Sigg et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0236212 A1* | 11/2004 | Jones et al. .............. 600/431 |
| 2004/0236213 A1 | 11/2004 | Jones et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0112151 A1 | 5/2005 | Horng |
| 2005/0113659 A1 | 5/2005 | Pothier et al. |
| 2005/0119562 A1 | 6/2005 | Jones et al. |
| 2005/0142161 A1 | 6/2005 | Freeman et al. |
| 2005/0143650 A1 | 6/2005 | Winkel |
| 2005/0165305 A1* | 7/2005 | Foerster et al. .............. 600/431 |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0216018 A1 | 9/2005 | Sennett |
| 2005/0234336 A1* | 10/2005 | Beckman et al. .............. 600/431 |
| 2005/0268922 A1 | 12/2005 | Conrad et al. |
| 2005/0273002 A1* | 12/2005 | Goosen et al. .............. 600/414 |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0025795 A1 | 2/2006 | Chesbrough et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0116573 A1 | 6/2006 | Field et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |

(56) References Cited

U.S. PATENT DOCUMENTS

| | | |
|---|---|---|
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0033280 A1 | 2/2008 | Lubock et al. |
| 2008/0065218 A1 | 3/2008 | O'Neil |
| 2008/0091120 A1 | 4/2008 | Fisher |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0093714 A1 | 4/2009 | Chesbrough et al. |
| 2009/0131825 A1 | 5/2009 | Burbank et al. |
| 2009/0171198 A1 | 7/2009 | Jones et al. |
| 2010/0010341 A1 | 1/2010 | Talpade et al. |
| 2010/0030072 A1 | 2/2010 | Casanova et al. |
| 2010/0030149 A1 | 2/2010 | Carr, Jr. |
| 2011/0184280 A1 | 7/2011 | Jones et al. |
| 2012/0078092 A1 | 3/2012 | Jones et al. |
| 2012/0116215 A1 | 5/2012 | Jones et al. |

FOREIGN PATENT DOCUMENTS

| | | |
|---|---|---|
| EP | 0255123 A2 | 2/1988 |
| EP | 0292936 A2 | 11/1988 |
| EP | 0458745 A1 | 11/1991 |
| EP | 0475077 A2 | 3/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| FR | 2853521 A1 | 10/2004 |
| GB | 708148 | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9608208 A1 | 3/1996 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Johnson & Johnson: Breast Biopsy (minimally invasive): Surgical Technique: Steps in the MAMOTOME Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: MAMMOTOME Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large—Tissue Engineering", Biotechnol. Prog., vol. 14, No. 1, pp. 134-140, 1998.

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Kochan, Jeffrey P., MD, "Interventional Neuroradiology: Current Practices and Techniques At Temple University Hospital", copied Apr. 30, 2002 from http://www.temple.edu/radiology/stroke.html, 2002, pp. 1-5.

Illanes, Teresa, "Synthesis of Novel Degradable Polymers for Tissue Engineering by Radical Polymerization" Degree Project in Polymer Technology, 2010, pp. 1-20, Stockholm, Sweden.

Konez, Orhan, MD, "Vascular Lesion Embolization Imaging" http://emedicine.medscape.com/article/419614-overview, Medscape Reference Drugs Diseases & Procedures, Apr. 11, 2011, pp. 1-18, WebMD.

International Search Report for PCT/US2009/000945 mailed Jul. 16, 2009.

Written Opinion of the International Searching Authority for PCT/US2009/000945 mailed Jul. 16, 2009.

International Search Report for PCT/US2007/016902 mailed Feb. 28, 2008.

(56) References Cited

OTHER PUBLICATIONS

International Search Report for PCT/US2007/016902 mailed Feb. 4, 2009.

Written Opinion of the International Searching Authority for PCT/US2007/016902 mailed Feb. 4, 2009.

International Search Report for PCT/US2007016918 mailed Nov. 26, 2007.

Written Opinion of the International Searching Authority for PCT/US2007016918 mailed Feb. 4, 2009.

Collagen—Definitions from Dictionary.com.

Fibrous—Definitions from Dictionary.com.

* cited by examiner

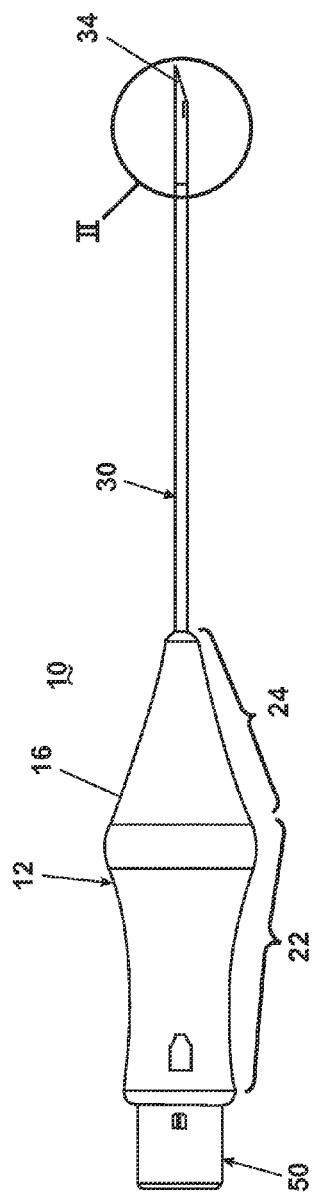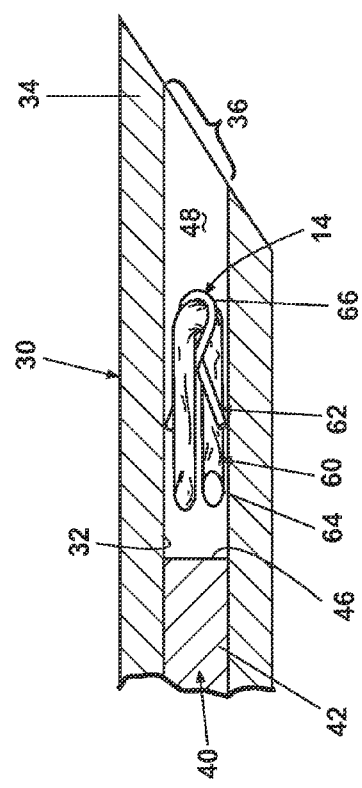

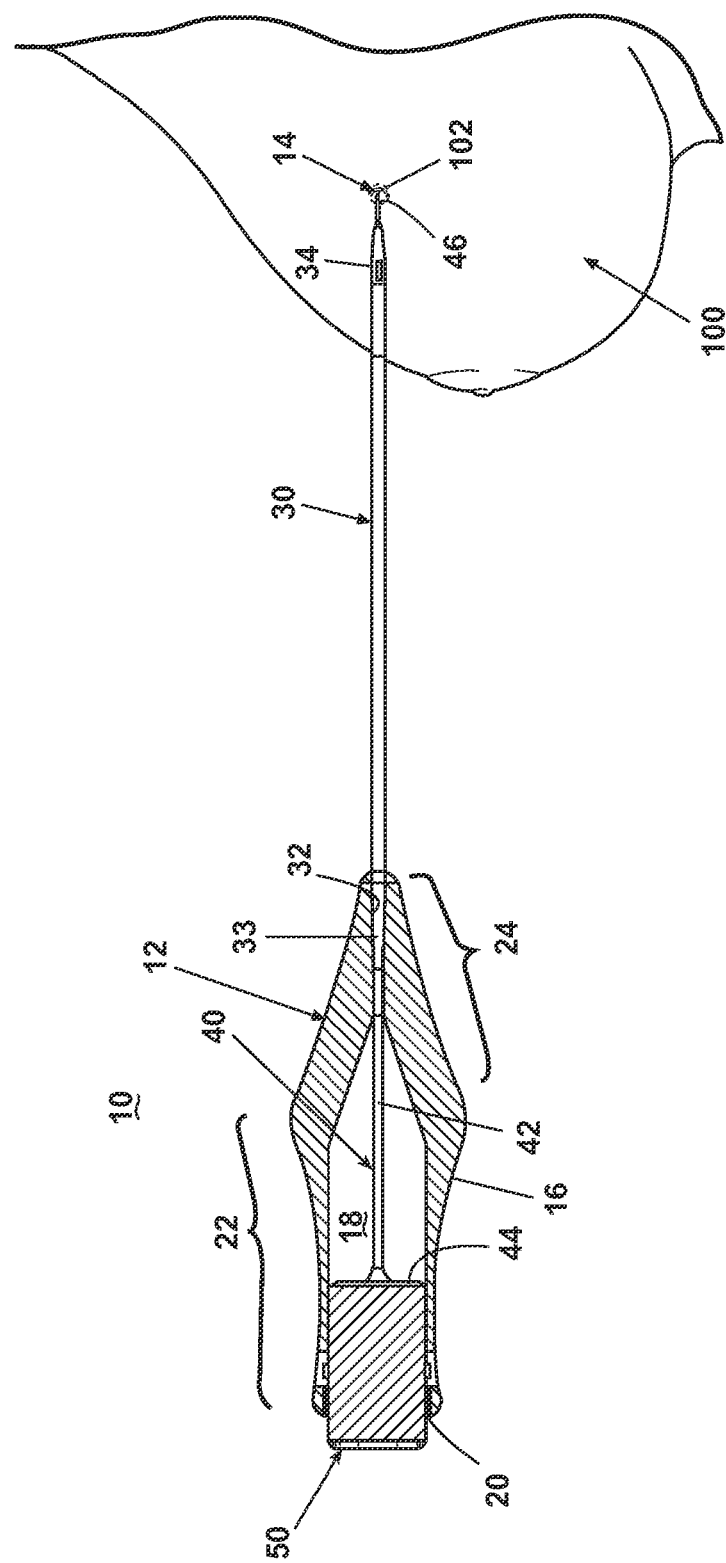

MULTI MODE IMAGING MARKER

CROSS-REFERENCE TO RELATED APPLICATIONS

This application is a continuation of U.S. application Ser. No. 10/709,899, filed Jun. 4, 2004, now abandoned, and a continuation-in-part of U.S. application Ser. No. 10/707,044, filed Nov. 17, 2003, now U.S. Pat. No. 7,424,320 B2, both of which are incorporated herein by reference in their entirety.

BACKGROUND OF THE INVENTION

1. Field of the Invention

The invention relates generally to a device for percutaneously implanting an imaging marker for identifying a location within a tissue mass. More particularly, the invention relates to a device for implanting a subcutaneous imaging marker that comprises at least two elements, each of which have a primary imaging mode.

2. Description of the Related Art

Subcutaneous imaging markers are commonly implanted to identify a particular location in various areas and organs of the body. For example, markers are positioned at biopsy sites so that a practitioner can readily identify the tissue sample location after the biopsy procedure is completed. Markers are also used to denote the locations of lesions for therapeutic procedures, such as chemotherapy.

Once the marker is implanted, it can be viewed using several well-known medical imaging techniques, such as radiography, ultrasonography, and magnetic resonance imaging (MRI). In radiography, x-rays, which are wavelike forms of electromagnetic energy carried by particles called photons, passed through the body are either scattered, absorbed, or transmitted by the hard and soft tissues. Hard tissues are more likely to absorb the x-ray photons, while the soft tissues tend to transmit the x-ray photons. The transmitted photons are recorded by a detector, such as an x-ray photographic film or a digital receiver, which produces a two-dimensional negative film image. Consequently, bones and other hard tissues appear white in the image, and organs, muscles, and other soft tissues appear black or gray. Mammography is a form of radiography where low dose x-ray photos are passed through a breast under compression to diagnose breast disease in women. In computerized axial tomography (CAT), another form of radiography, the x-ray source and the x-ray detectors revolve around the body, or the source remains stationary, and the x-ray beam is bounced off a revolving reflector. A machine records x-ray slices across the body in a spiral motion. After the patient passes through the machine, the computer combines all the information from each scan to form a three-dimensional detailed image of the body.

Ultrasonography involves emitting a beam of high frequency, about 3-10 MHz, pulses of acoustic energy from a transmitter and onto body tissue surfaces oriented perpendicular to the transmitter. Some of the acoustic energy pulses reflect at boundaries between tissues having a difference in acoustic impedance, which is a medium's resistance to transmission of acoustic energy, and the echo is detected by an acoustic transducer, which transforms the echo into an electrical pulse. Some of the energy transmits past the boundary until it reaches another boundary where it can reflect back to the transducer. The electric pulse is sent to a computer with a display, and the computer forms a two-dimensional image by determining the proper location of a dot, and its corresponding shade of gray, on the display screen. As the difference in acoustic impedance at a boundary increases, more sound energy is reflected. Body tissue has an acoustical impedance over 3000 times that of air; consequently, entrapped air can be used in subcutaneous imaging markers in order to enhance the visibility of the marker during ultrasonography. Additionally, the texture of the marker can increase the scattering of the acoustical energy pulses.

In MRI, the patient is positioned inside a strong magnetic field usually generated by a large bore superconducting magnet. Specifically, the body part to be scanned is placed in the exact center or isocenter of the magnetic field, and the MRI scanner takes several slices that can be combined to form two-dimensional images or three-dimensional models. Markers comprising non-magnetic materials are viewable with MRI.

Generally speaking, markers have several imaging modes where they can be viewed with any of the above imaging techniques; however, each marker has a primary imaging mode wherein the marker is best viewed or most easily distinguished. For example, a metal clip having a simple, thin shape can be difficult to discern with ultrasonography if the marker is oriented on its side relative to the acoustic emitter. On the display, which is typically grainy, the marker will appear as a very thin, undistinguishable line. On the other hand, such a marker is readily seen with x-ray, regardless of its orientation, because of the sharp contrast in x-ray transmission between the metal and the surrounding soft tissue. Accordingly, the metal marker has an ultrasound imaging mode and an x-ray imaging mode, and the x-ray imaging mode is the primary imaging mode. Other markers, such as those with entrapped air, can be seen easily with ultrasonography but are not as visible in an x-ray imaging mode because they transmit the x-ray photons in a manner similar to the soft tissue. Such markers also have an ultrasound imaging mode and an x-ray imaging mode, but the primary imaging mode is the ultrasound imaging mode. In selecting a marker, a practitioner is most likely to choose a marker that has a primary imaging mode corresponding to a preferred imaging technique. However, such a selection can preclude the effective use of other imaging techniques. For example, in some procedures the marker is permanent and will be imaged multiple times by different technicians over a relatively long time span, possibly over several years. During that time, different imaging techniques might be used. Thus, it is desirable for a marker to have multiple primary modes.

SUMMARY OF THE INVENTION

According to the invention, an imaging marker for the subcutaneous marking of tissue comprises a first non-bioabsorbable element having a first primary imaging mode and a second non-bioabsorbable element having a second primary imaging mode. The second primary imaging mode is different than the first primary imaging mode.

The first primary imaging mode is one of ultrasound, x-ray, CAT, and MRI, and the second primary imaging mode is one of ultrasound, x-ray, CAT, and MRI. One of the first and second primary imaging modes can be ultrasound and the other of the first and second primary imaging modes can be x-ray.

The first non-bioabsorbable element is expandable in volume and made from PVA. The second non-bioabsorbable element is made of metal. At least a portion of one of the first and second non-bioabsorbable elements is embedded in the other of the first and second non-bioabsorbable elements. One of the first and second non-bioabsorbable elements can be completely embedded in the other of the first and second non-bioabsorbable elements.

The first non-bioabsorbable element comprises a loop that surrounds the second non-bioabsorbable element.

The first non-bioabsorbable element comprises a body with a foot, and the foot can form an anchor. The body can be embedded within the second non-bioabsorbable element, and the foot can be embedded within the second non-bioabsorbable element.

In another aspect, an imaging marker according to the invention for the subcutaneous marking of tissue comprises a metal element and a PVA element, wherein the metal element and PVA element form a composite body.

At least a portion of one of the metal and the PVA elements is embedded in the other of the metal and the PVA elements, and one of the metal and the PVA elements can be completely embedded in the other of the metal and the PVA elements.

The metal element comprises a head with an anchor. The head can be embedded within the PVA element. The metal element can comprise a loop from which extends at least one foot, with the loop surrounding the PVA element to form the head and the at least one foot forming the anchor. The loop has an inner diameter and the PVA element has an outer diameter, wherein the PVA element can expand so that the outer diameter is greater than the inner diameter to effect embedding of the one of the metal and the PVA elements in the other of the metal and the PVA elements. The inner diameter can be between 0.010 and 0.030 inches, and the outer diameter can be expanded to approximately twice the inner diameter. The PVA element can be folded against the at least one foot so that the composite body is sized to be received within a hollow needle having a gauge of less than 20. The PVA element can be compressed to be sized for receipt within the hollow needle.

According to the invention, a marking device for percutaneously implanting an imaging marker comprises a cannula defining a lumen and having a distal end and an expulsion opening near the distal end; a stylet slidably received within the lumen for movement between a ready position in which a tip of the stylet is spaced inwardly from the distal end to form a marker recess therebetween, and an extended position in which the tip of the stylet is advanced toward the distal end; and an imaging marker comprising a first non-bioabsorbable element having a first primary imaging mode, and a second non-bioabsorbable element having a second primary imaging mode, wherein the second primary imaging mode is different than the first primary imaging mode. Movement of the stylet from the ready position to the extended position thereby ejects the imaging marker from the marker recess through the expulsion opening.

The marking device further comprises a handle to be grasped by a user, and the cannula has a proximal end mounted to the handle. Further, the marking device comprises an actuator for moving the stylet relative to the cannula. The actuator is mounted to the handle and is a plunger movable between a first position and a second position for moving the stylet between the ready position and the extended position.

The cannula, the stylet, the actuator, and the handle form an introducer, and the introducer and the imaging marker form a self-contained marking device that can be easily and conveniently handled by a user to place the imaging marker at a predetermined location in a tissue mass by the user moving the plunger between the first and second positions to move the stylet from the ready to the extended position to thereby eject the imaging marker from the marker recess after the cannula is inserted into the tissue mass and the insertion tip is located at the predetermined location.

The first primary imaging mode is one of ultrasound, x-ray, CAT, and MRI, and the second primary imaging mode is one of ultrasound, x-ray, CAT, and MRI. One of the first and second primary imaging modes is ultrasound, and the other of the first and second primary imaging modes is x-ray.

The first non-bioabsorbable element is expandable in volume. The first non-bioabsorbable element is made from PVA, and the second non-bioabsorbable element is made of metal.

At least a portion of one of the first and second non-bioabsorbable elements is embedded in the other of the first and second non-bioabsorbable elements. The one of the first and second non-bioabsorbable elements can be completely embedded in the other of the first and second non-bioabsorbable elements.

The first non-bioabsorbable element comprises a loop that surrounds the second non-bioabsorbable element.

The first non-bioabsorbable element comprises a head with at least one foot. The body can be embedded within the second non-bioabsorbable element, and the at least one foot can be embedded within the second non-bioabsorbable element. The at least one foot can form an anchor.

BRIEF DESCRIPTION OF THE DRAWINGS

In the drawings:

FIG. 1 is a plan view of an introducer used to place an imaging marker at a predetermined location in accordance with the invention;

FIG. 2 is an enlarged sectional view of the area II of FIG. 1, illustrating a first embodiment of an imaging marker according to the invention comprising a clip and a cylinder, wherein the cylinder is in a folded and compressed condition, within a marker recess portion of the introducer prior to ejection;

FIG. 3 is a plan view of the introducer of FIG. 1, wherein the introducer has ejected the imaging marker into a tissue mass;

DESCRIPTION OF THE INVENTION

Figure 4:
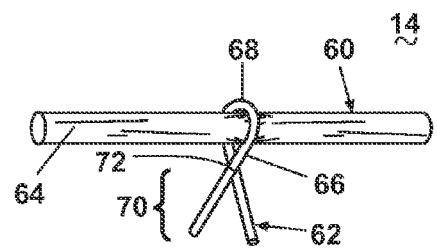
FIG. 4 is an enlarged perspective view of the imaging marker of FIG. 2, illustrating the cylinder of the imaging marker in a straight configuration.

The invention addresses the deficiencies of the prior art and provides a marking device for percutaneously implanting an imaging marker comprising at least two elements, wherein each element has a primary imaging mode different from the primary imaging modes of the other elements.

Referring now to the figures, FIGS. 1 to 3 illustrate a marking device 10 according to the invention, which is capable of the percutaneous placement of an imaging marker at a predetermined location, such as a biopsy site or a lesion, within a tissue mass 100. The marking device 10 comprises an introducer 12 and an imaging marker 14 (FIG. 2) contained within the introducer 12. The introducer 12 includes a handle 16 having a hollow interior 18 and a rear opening 20. The handle 16 comprises a grip portion 22 from which extends a tapered nose portion 24.

The tapered nose portion 24 houses a press-fit cannula 30, which defines a lumen 32. The cannula 30 comprises a proximal end 33 mounted to the handle 16 and a distal end 34 having an expulsion opening 36 spaced from the handle 16. Preferably, the cannula 30 has a gauge of less than 20, and a 17-gauge (0.058 inch outer diameter) cannula, with an inner diameter ranging from 0.049 to 0.051 inches, is most preferred. Optionally, the distal end 34 of the cannula 30 can be sharpened to facilitate insertion through the tissue mass 100. Furthermore, the distal end 34 of the cannula 30 can be designed for enhanced visibility using common imaging techniques, such as radiography, ultrasonography, and magnetic resonance imaging (MRI). Suitable cannula tips are disclosed in U.S. Pat. No. 5,490,521, issued Feb. 13, 1996 to R. E. Davis and G. L. McLellan, which is incorporated by reference. Ultrasound enhancement technology is also disclosed in U.S. Pat. No. 4,401,124, issued Aug. 30, 1983 to J. F. Guess et al.; and U.S. Pat. No. 4,582,061, issued Apr. 15, 1986 to F. J. Fry.

A stylet 40 comprising a base 44 and shaft 42 with a tip 46 is slidably received within the hollow interior 18 of the handle 16 in a manner such that the shaft 42 extends into the cannula lumen 32 and the stylet base 44 lies within the hollow interior 18. An actuator in the form of a plunger 50 in operable communication with the stylet base 44 comprises a cylindrical body sized so that it is slidably received within the rear opening 20 of the handle 16. Linear displacement of the plunger 50 within the rear opening 20 correspondingly shifts the stylet 40 relative to the handle 16 and the cannula 40.

The stylet 40 is movable between a ready position, as best seen in FIG. 2, and an extended position, as illustrated in FIG. 3. In the ready position, the tip 46 of the stylet 40 is spaced inwardly from the distal end 34 of the cannula 30 to form a marker recess 48 sized to receive the imaging marker 14. When the stylet 40 moves to the extended position, the tip 46 advances towards the distal end 34 to reduce the volume of the marker recess 48 and thereby eject the marker 14 from the marker recess 48. It is preferred that the stylet shaft 42 be sized in a manner such that when the plunger 50 is in the extended position, the stylet shaft 42 extends beyond the distal end 34 of the cannula 30 to ensure complete ejection of the imaging marker 14 from the marker recess 48. Movement of the plunger 50, which operably engages the stylet base 44, from a first position (FIG. 1) and towards the handle 16 to a second position (FIG. 3) shifts the stylet 40 from the ready position to the extended position.

Further details of the introducer 12 are provided in U.S. Pat. No. 6,575,991, issued Jun. 10, 2003 to R. M Chesbrough et al., which is incorporated herein by reference.

It will be recognized that the foregoing construction provides a self-contained marking device, which may be preassembled as a unit and prepackaged, all under sterile conditions, thereby affording the practitioner substantially greater convenience and reliability.

Referring now to FIG. 4, a first embodiment of the imaging marker 14 according to the invention comprises a first element 60 and a second element 62 that form a composite body. The first element 60 has several imaging modes. That is, the first element can be imaged by different imaging techniques. Each imaging mode corresponds to a different imaging technique, including, but not limited to, radiography, such as standard x-ray, mammography, and computerized axial tomography (CAT), ultrasonography, and MRI. However, not all imaging modes have the same efficacy. The first element 60 is not necessarily easily viewable in each of the imaging modes and could even be substantially indistinguishable from the surrounding tissue in one or more of the imaging modes. Conversely, in at least one of the imaging modes, which will be referred to as a primary imaging mode, the first element 60 is most readily viewed and easily discernable with a particular imaging technique when located in the tissue mass 100. For example, the first element 60 can have imaging modes wherein it is viewable with, for example, x-ray, MRI, and ultrasound. If the first element 60 is especially viewable with ultrasound, then, of all the imaging modes, the primary imaging mode for the first element 60 is an ultrasound imaging mode.

Similar to the first element 60, the second element 62 has several imaging modes and, in at least one of the imaging modes, which is the primary imaging mode, the second element 62 is most readily viewed and easily discernable with a particular imaging technique when located in the tissue mass 100. For example, the second element 62 can have imaging modes wherein it is viewable with, for example, x-ray, MRI, and ultrasound. If the second element 62 is especially viewable with x-ray, then, of all the imaging modes, the primary imaging mode for the second element 62 is an x-ray imaging mode. However, the primary imaging mode of the second element 62 is different than the primary imaging mode of the first element 60. Because the first and second elements 60 and 62 have different primary imaging modes, the imaging marker 14 has at least two different primary imaging modes and, therefore, can be readily viewed and distinguished from the surrounding tissue with at least two different imaging techniques. For example, if the first and second elements 60 and 62 have primary imaging modes corresponding to ultrasound and x-ray, respectively, then the subcutaneous imaging marker 14 can be identified with both ultrasound and x-ray imaging techniques.

The imaging marker 14 can optionally comprise other elements in addition to the first and second elements 60 and 62, wherein each of the other elements has its own primary imaging mode. For example, the imaging marker can comprise a third element having a third primary imaging mode, a fourth element having a fourth primary imaging mode, and so on. The primary imaging mode of each of the other elements can be unique, can be the same as each other, and can be the same as the first or second primary imaging modes. For example, if the imaging marker comprises three elements, wherein the first primary imaging mode is ultrasound and the second primary imaging mode is x-ray, the third primary imaging mode can be ultrasound, x-ray, or another imaging mode, such as MRI.

Each element of the imaging marker 14 is considered to be a fundamental constituent thereof. An element that is modified to enhance an imaging mode other than its primary imaging mode is considered to constitute more than one element. For example, if a first element having a first primary imaging mode is coated so that it is readily viewed and easily discernable with an imaging technique other than that corresponding to the first imaging mode, then the coating is considered to be a second element with a second primary imaging mode. Other examples of modifying elements include adding texture to a surface of an element; immersing an element in a material for impregnation thereof, and blowing air into an element to form pockets or pores of air. In these examples, the texture, the material, and the air are considered to be fundamental constituents of the imaging marker and separate elements having their own primary imaging modes.

The first element 60 is composed of a biocompatible, non-bioabsorbable, and flexible material, preferably polyvinyl alcohol (PVA). Additionally, the first element has a compressible and expandable form, for example, a sponge-like element comprising several small pores (not shown) that undergoes a volumetric change during compression or expansion. When the first element 60 is outside the body, the pores are filled with gas, such as air. In this state, the sponge-like form is easily compressed such that the overall volume of the first element 60 reduces. Conversely, when the first element 60 is introduced into the tissue mass 100, water and other liquids from the tissue enter the pores and thereby swell or expand the first element 60 to a larger volume. Not all of the gas leaves the sponge-like form upon expansion and the absorption of liquid. Some air pockets remain and are readily visible with ultrasound. The combination of the texture, structure, and air pockets of the sponge-like form renders the first element 60 most readily viewable with ultrasound when disposed in the tissue mass 100. Correspondingly, the preferred primary imaging mode of the first element 60 is an ultrasound imaging mode.

The second element 62 is composed of a biocompatible, non-bioabsorbable, and substantially rigid material, preferably a metal, including, but not limited to, titanium and stainless steel. Metals have a significantly lower x-ray transmission relative to soft tissue and, therefore, are clearly distinguishable from surrounding tissue with radiographic imaging techniques, regardless of the orientation of the second element 62. Consequently, the preferred primary imaging mode of the second element 62 is a radiographic imaging mode, such as an x-ray imaging mode. It follows that the imaging marker 14 implanted into the tissue mass 100 can be clearly and consistently viewed with both ultrasonography and radiography, such as x-ray.

The imaging marker 14 can optionally be modified to incorporate another element. For example, the first element 60 can be soaked in a material, such as iodine or gadolinium, that is viewable with an imaging technique. Iodine and gadolinium are exemplary materials that are known to be viewable with MRI. During the soaking process, the material impregnates the first element 60 and renders the imaging marker 14 viewable with MRI. Consequently, the imaging marker 14 with the first element 60 impregnated with the material comprises a third element, which is the material, having a third primary imaging mode, which is MRI.

With continued reference to the first embodiment shown in FIG. 4, the first element 60 is in the shape of an elongated cylinder 64 with an outer diameter, and the second element 62 is a clip 66 with a head 68 and a pair of feet 70. The head 68 and feet 70 are separated by a region 72 where the clip 62 crosses over itself. The head 68 forms a loop, with an inner diameter, that receives the cylinder 64, and the feet 70 function as anchors to secure the imaging marker 14 within the tissue mass 10 and prevent migration after implantation.

The cylinder 64 can be flexed from a straight configuration, as illustrated in FIG. 4, to a folded condition, as shown in FIG. 2, so that the imaging marker 14 is sized to be received within the lumen 32 of the cannula 30. In the folded condition, the cylinder 64 is bent near its center into somewhat of a U-shape. In particular, the cylinder is folded substantially in half against the cross region 72 and the feet 70 of the clip 66. The ends of the cylinder 64 preferably extend beyond the feet 70. Additionally, the feet 70 of the clip 66 can be squeezed together slightly, if necessary, to fit the imaging marker 14 within the lumen 32.

While the inner diameter of the head 68 is substantially fixed, the outer diameter of the cylinder 64 can significantly alter during compression or expansion. To facilitate insertion of the cylinder 64 through the head 68, as illustrated in FIG. 4, the first element 64 can be compressed, if necessary, to reduce the outer diameter so that it is less than inner diameter of the head 68. Furthermore, the first element 64 can be compressed to fit the imaging marker 14 within the marker recess 48.

When the cylinder 64 absorbs liquid and expands, the outer diameter increases, preferably to a dimension greater than the inner diameter of the head 68. Because the cylinder 64, in the expanded condition, is larger than the head 68, the head 68 effectively pinches the cylinder 64 near its center, as best viewed in FIG. 6, and the two elements 60 and 62 exert opposing forces upon each other and become embedded. As a result of the embedding, the two elements 60 and 62 form a bond that prevents separation of the cylinder 64 from the clip 66.

Exemplary dimensions of the first and second elements 60 and 62 for the first embodiment of the imaging marker 14 will now be presented. These dimensions are for illustrative purposes and are not meant to limit the invention in any manner. It is well within the scope of the invention for the dimensions of the first and second elements 60 and 62 to differ from those provided hereinafter provided that the imaging marker is sized to be received within the cannula 30, regardless of the size thereof. As stated above, the cannula 30 is preferably less than 20 gauge, and a 17-gauge cannula with a 0.049 to 0.051 inch inner diameter is preferred. The cannula 30, however, is not limited to this size, and, thus, the dimensions of the imaging marker 14 shall not be limited in a similar manner.

Preferably, the cylinder 64 has a length and outer diameter of 0.315 and 0.040 inches, respectively. The height of the clip 66 is preferably 0.120 inches, and the width of the clip 66 at the feet 70 is 0.055 inches and at the head 68 is 0.045 inches. Additionally, the inner diameter of the head 68 is preferably 0.021 inches. It is apparent that, for the imaging marker 14 with the above dimensions, the cylinder 64 of must be compressed for insertion through the head 68 and that expansion of the cylinder 64 to its original size or larger will cause embedding of the first and second elements 60 and 62.

The above exemplary dimensions are preferred and are suitable for an imaging marker that can be uses in a hand-held marking device with a 20-gauge or less cannula. Such hand-held devices are relatively small and less invasive when compared to other systems, such as the Mammotome® Breast Biopsy System. However, it is within the scope of the invention to alter the dimensions of the imaging marker so that it can be used with larger, non-hand-held systems.

Referring now to FIGS. 1-3 and FIGS. 5 and 6, in operation, the introducer 12 begins with the stylet 40 in the ready position (FIG. 2) and the plunger 50 in the first position (FIG. 1). With the introducer 12 in this condition, the cannula 30 is positioned so that its distal end 34 is at or near the predetermined location, which is illustrated as a biopsy site 102 in FIGS. 3, 5, and 6, in the tissue mass 100. Preferably, the distal end 34 of the cannula 30 is positioned by using a suitable imaging system.

Figure 5:
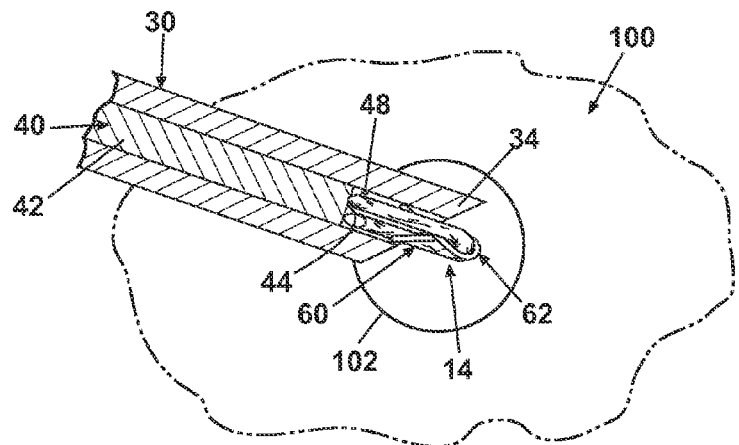
FIG. 5 is an enlarged partial sectional view of the imaging marker of FIG. 2 partially ejected from the introducer into a biopsy site.

Once the cannula 30 is positioned at the predetermined location, the plunger 50 is moved from its first position to the second position to displace the stylet 40 from the ready position to the extended position, as shown in FIG. 3. As the plunger 50 moves, it drives the stylet base 44 forward to advance the stylet shaft 42 within the lumen 32. As the stylet shaft 42 progresses through the lumen 32, the tip 46 pushes the imaging marker 14 through the marker recess 48 such that the imaging marker 14 extends from the distal end 34 of the cannula, as illustrated in FIG. 5. When the stylet shaft 42 is fully advanced, the imaging marker 14 is completely ejected from the marker recess 48 and is disposed at the predetermined location within the tissue mass 100.

During the ejection process, the tissue mass 100 can resist the advancement of the imaging marker 14. PVA in a sponge-like form is relatively weak, thus making it difficult for first element 60 to push through the tissue mass on its own. Because the second element 62 is composed of metal, it dominates the resistive forces from the tissue mass 100 and delivers the first element 60 to the predetermined location. As the imaging marker 14 advances through the marker recess 48 and into the tissue mass 100, the cross region 72 of the clip 66 pulls the cylinder 64, which is in the folded condition, along with the clip 66 to the predetermined location.

Figure 6:
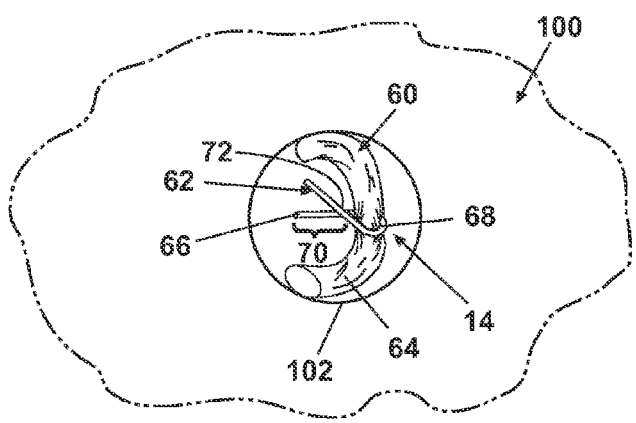
FIG. 6 is an enlarged plan view of the imaging marker of FIG. 2 completely disposed within a biopsy site and wherein the cylinder is in an unfolded and expanded condition.

As depicted in FIG. 6, the cylinder 64, upon ejection, unfolds and expands as it absorbs liquid from the tissue mass 100. The degree to which the cylinder 64 unfolds is governed by the geometry and structure of the predetermined location. If the predetermined location is a biopsy site 102 having a dimension larger than the length of the cylinder 64, then typically the cylinder 64 will unfold until it becomes constrained by the cavity walls of the biopsy site 102. Upon expansion, the cylinder 64 and the head 68 become embedded, thereby securing the first and second elements 60 and 62 together. Additionally, the feet 70 anchor the imaging marker 14 to the predetermined location to prevent migration of the imaging marker 14 within the tissue mass 100.

After implantation, the subcutaneous imaging marker 14 is easily viewed in either of the primary imaging modes of the first and second elements 60 and 62. A practitioner can identify the imaging marker 14 and, therefore, pinpoint the predetermined location using either ultrasound, which is the primary imaging mode of the first element 60, or x-ray, which is the primary imaging mode of the second element 62. As a result of the ability to clearly view the imaging marker 14 with multiple imaging techniques, the practitioner has the luxury of being able to select the imaging technique most suitable for the patient.

Alternative embodiments of the imaging marker 14 according to the invention are illustrated in FIGS. 7-10 where similar components are identified with the same reference numeral bearing a prime (') symbol. The alternative embodiments are substantially the same as the first embodiment, with the primary difference being the form of the second element 62 and the manner in which it is coupled to the first element 60.

In general, the alternative embodiments of an imaging marker 14' comprise a first element 60' and a second element 62'. As in the first embodiment, the second element 62' is preferably a clip 66' with a head 68' and a pair of feet 70' separated by a cross region 72'. The first element 60', on the other hand, comprises various forms, as depicted in FIGS. 7-10. Regardless of the form of the first element 60', at least a portion of each of the first and second elements 60' and 62' are embedded to secure the elements 60' and 62' together to form a composite body.

Figure 7:
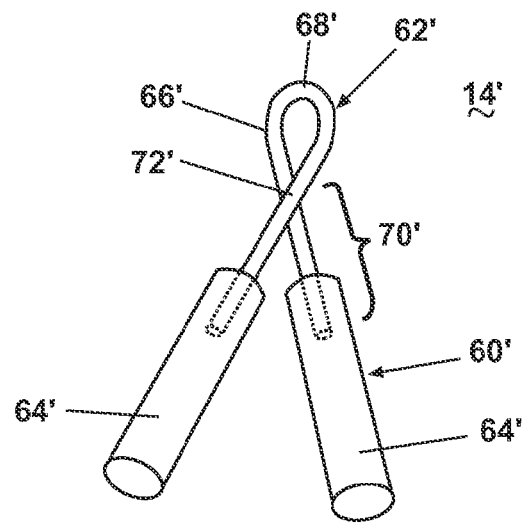
FIG. 7 is an enlarged perspective view of a second embodiment of an imaging marker according to the invention.

In a second embodiment of the imaging marker 14' shown in FIG. 7, the first element 60' is in the form of two cylinders 64' mounted onto the feet 70' of the clip 66'. Preferably, an adhesive, such as an ultraviolet (UV) curable adhesive, facilitates the mounting the cylinders 64'. An example of a UV curable adhesive is a cyanoacrylate adhesive. The head 68' of the second embodiment functions as an anchor to prevent migration of the imaging marker 14'.

Figure 8:
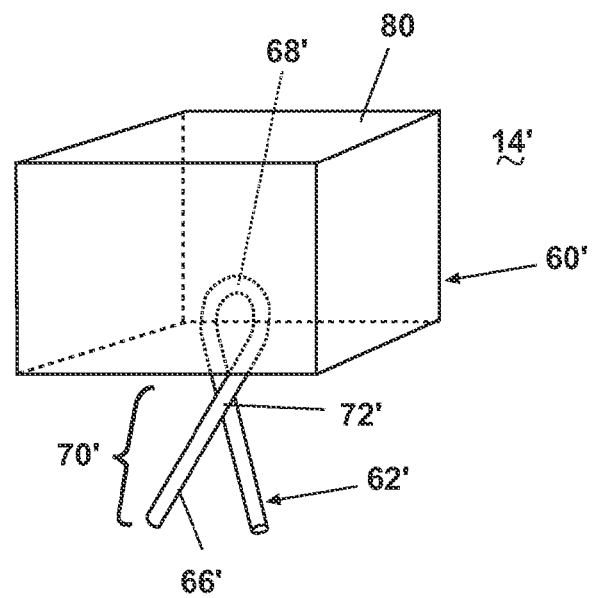
FIG. 8 is an enlarged perspective view of a third embodiment of an imaging marker according to the invention.
Figure 9:
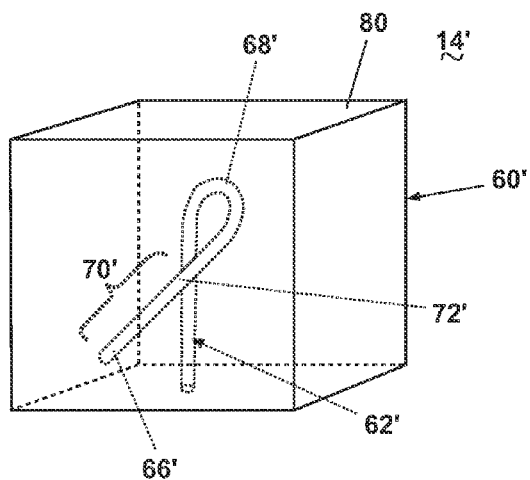
FIG. 9 is an enlarged perspective view of a fourth embodiment of an imaging marker according to the invention.
Figure 10:
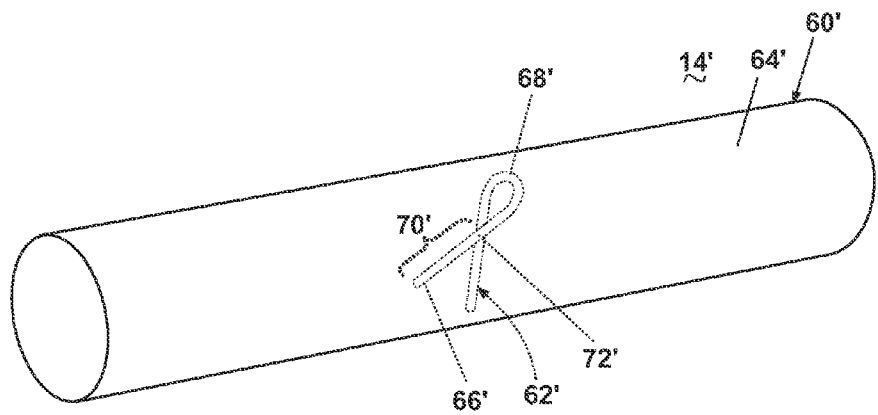
FIG. 10 is an enlarged perspective view of a fifth embodiment of an imaging marker according to the invention.

The first element 60' of third and fourth embodiments, which are illustrated in FIGS. 8 and 9, is in the form of a block 80. In the third embodiment, the head 68' of the clip 66' is embedded within the block 80, while the entire clip 66' is embedded in the block 80 in the fourth embodiment. In a fifth embodiment, the clip 66' is also completely embedded within the first element 60', but the first element 60' is in the form of a cylinder 64'.

The alternative embodiments in FIGS. 7-10 are ejected from the marker recess 48 of the marking device 10 and into the predetermined location within the tissue mass 100 in the same manner as the first embodiment. After implantation, the imaging markers 14' can be clearly viewed and distinguished from the surrounding tissue with imaging techniques corresponding to the primary imaging modes of the first and second elements 60' and 62'.

While the imaging marker is described above as comprising two non-bioabsorbable elements, each with a different primary imaging mode, the invention shall not be limited to comprising only two non-bioabsorbable elements. It is within the scope of the invention for the imaging marker to comprise more than two non-bioabsorbable elements, each with a different primary imaging mode. Further, each non-bioabsorbable element can have more than one primary imaging mode provided that one of the primary imaging modes is different from the primary imaging mode(s) of the other element(s). For example, if the second element is comprised of a non-magnetic metal, such as titanium, and can be viewed with MRI as well as with x-ray, then the second element could have two primary imaging modes.

In the five embodiments presented herein, the first element is the form of a cylinder or block, and the second element is shown as a clip; however, the first and second elements can be of any suitable shape that can be received within the cannula and implanted into a tissue mass. Additionally, the imaging marker is not limited to use with the marking device detailed above. The imaging marker can be implanted with a device that is not self-contained or with a self-contained marking device other than that described herein.

The imaging marker according to the invention can be easily viewed and readily distinguished from the surrounding tissue with more than one medical imaging technique. Because a practitioner is not limited to locating the imaging marker with only one technique, he or she has the flexibility of being able to select the imaging technique most suitable, both physically and financially, for the patient. Furthermore, the non-bioabsorbable imaging marker is securely embedded together and anchored to the predetermined location to provide a reliable and enduring marker for the predetermined location.

While the invention has been specifically described in connection with certain specific embodiments thereof, it is to be understood that this is by way of illustration and not of limitation, and the scope of the appended claims should be construed as broadly as the prior art will permit.

We claim:

1. An imaging marker for the subcutaneous marking of tissue, the imaging marker comprising:
   a composite body configured for delivery through a cannula of a marker introducer, wherein the composite body includes a first non-bioabsorbable article and a second non-bioabsorbable article, wherein the first non-bioabsorbable article is secured the second non-bioabsorbable article with direct contact between the first non-bioabsorbable article and the second non-bioabsorbable article;
   wherein the first non-bioabsorbable article is a rigid article viewable via a first primary imaging mode and wherein the second non-bioabsorbable article is a flexible article viewable via a second primary imaging mode that is different from the first primary imaging mode, wherein the rigid article comprises a head with an anchor, and wherein the rigid article comprises a loop from which extends at least one foot, with the loop surrounding an outer surface of the flexible article to form the head and the at least one foot forming the anchor.

2. The imaging marker of claim 1 wherein the loop has an inner diameter and the flexible article has an outer diameter, wherein the flexible article is configured to expand so that the outer diameter is greater than the inner diameter to effect embedding of the rigid article in the flexible article.

3. The imaging marker of claim 2 wherein the inner diameter is between 0.010 and 0.030 inches.

4. The imaging marker of claim 1 wherein the flexible article is configured to be folded against the at least one foot so that the composite body is sized to be received within a hollow needle having a gauge of less than 20.

5. A composite tissue marker sized for delivery through a lumen of a cannula into a patient, comprising:

a first unitary non-bioabsorbable article having a securing portion; and a second unitary non-bioabsorbable article disposed adjacent to the securing portion of the first unitary non-bioabsorbable article, wherein the securing portion of the first unitary non-bioabsorbable article exerts a force on the second unitary non-bioabsorbable article to secure the first unitary non-bioabsorbable article to the second unitary non-bioabsorbable article to form the composite tissue marker, wherein the first unitary non-bioabsorbable article is a unitary metal article having the securing portion and the second unitary non-bioabsorbable article is a unitary non-bioabsorbable polymer article that is disposed adjacent to the securing portion of the unitary metal article, wherein the securing portion of the unitary metal article exerts the force on the unitary non-bioabsorbable polymer article to secure the unitary metal article to the unitary non-bioabsorbable polymer article to comprise the composite tissue marker, and wherein the securing portion of the unitary metal article forms a loop, and the unitary non-bioabsorbable polymer article is an elongate member having a first end and a second end, the elongate member being inserted into the loop, with the loop being positioned between the first end and the second end of the elongate member.

6. A composite tissue marker sized for delivery through a lumen of a cannula into a patient, comprising:

a first unitary non-bioabsorbable article having a securing portion; and a second unitary non-bioabsorbable article disposed adjacent to the securing portion of the first unitary non-bioabsorbable article, wherein the securing portion of the first unitary non-bioabsorbable article exerts a force on the second unitary non-bioabsorbable article to secure the first unitary non-bioabsorbable article to the second unitary non-bioabsorbable article to form the composite tissue marker, wherein the first unitary non-bioabsorbable article is a unitary metal article having the securing portion and the second unitary non-bioabsorbable article is a unitary non-bioabsorbable polymer article that is disposed adjacent to the securing portion of the unitary metal article, wherein the securing portion of the unitary metal article exerts the force on the unitary non-bioabsorbable polymer article to secure the unitary metal article to the unitary non-bioabsorbable polymer article to comprise the composite tissue marker, and wherein the securing portion of the unitary metal article includes a loop and the unitary non-bioabsorbable polymer article is a cylinder, the cylinder being positioned in the loop of the unitary metal article.

7. A composite tissue marker configured for percutaneous placement into tissue via an introducer cannula, the composite tissue marker comprising:

an elongate flexible non-bioabsorbable polyvinyl alcohol marker portion having an exterior; and a rigid non-bioabsorbable metallic marker portion secured to the elongate flexible non-bioabsorbable polyvinyl alcohol marker portion with direct contact between the rigid metallic non-bioabsorbable marker portion and the exterior of the elongate flexible non-bioabsorbable polyvinyl alcohol marker portion, wherein the rigid non-bioabsorbable metallic portion is a metal wire having a first end, a second end, and a mid-portion, the metal wire being configured to have a loop at the mid-portion, and with the elongate flexible non-bioabsorbable polyvinyl alcohol marker portion being securely received within the loop.

* * * * *